United States Patent [19]

Sitar

[11] Patent Number: 4,819,659
[45] Date of Patent: Apr. 11, 1989

[54] BLOOD WITHDRAWAL DEVICE WITH MOVABLE NEEDLE GUARD MEMBER

[75] Inventor: Dennis L. Sitar, Trabuco Canyon, Calif.

[73] Assignee: ICU Medical, Inc., Mission Viejo, Calif.

[21] Appl. No.: 99,331

[22] Filed: Sep. 21, 1987

[51] Int. Cl.$^4$ ............................................. A61B 5/00
[52] U.S. Cl. .................................... 128/764; 128/770; 604/198
[58] Field of Search ................. 128/763, 764, 770; 604/192, 196-198, 263

[56] References Cited

U.S. PATENT DOCUMENTS

| | | | |
|---|---|---|---|
| 2,559,474 | 7/1951 | Son | 604/263 |
| 3,123,073 | 3/1964 | Barr et al. | 128/764 |
| 3,734,080 | 5/1973 | Petterson et al. | 128/764 |
| 4,139,009 | 2/1979 | Alvarez | 604/198 |
| 4,444,203 | 4/1984 | Engelman | 128/763 |
| 4,679,571 | 7/1987 | Frankel et al. | 128/764 |
| 4,702,738 | 10/1987 | Spencer | 604/198 |

*Primary Examiner*—Max Hindenburg
*Attorney, Agent, or Firm*—Whann & Connors

[57] ABSTRACT

Disclosed is a blood withdrawing device including an elongated needle to which is bonded during molding a unitary polymeric structure. This unitary structure has a tube holding section and a locking section for locking a guard member in a permanently forward position which covers the tip of the needle. The guard member is mounted concentrically to the locking member and movable axially along the needl's shaft from a retracted position where the top of the needle is exposed and a forward position where the tip is covered. The locking member includes an elongated stem which is formed during the molding process. A second tip of the needle extends into the tube holding means and is displaced inwardly from an open mouth in the tube holding means which allows a vacuum tube to be inserted into the open mouth.

5 Claims, 2 Drawing Sheets

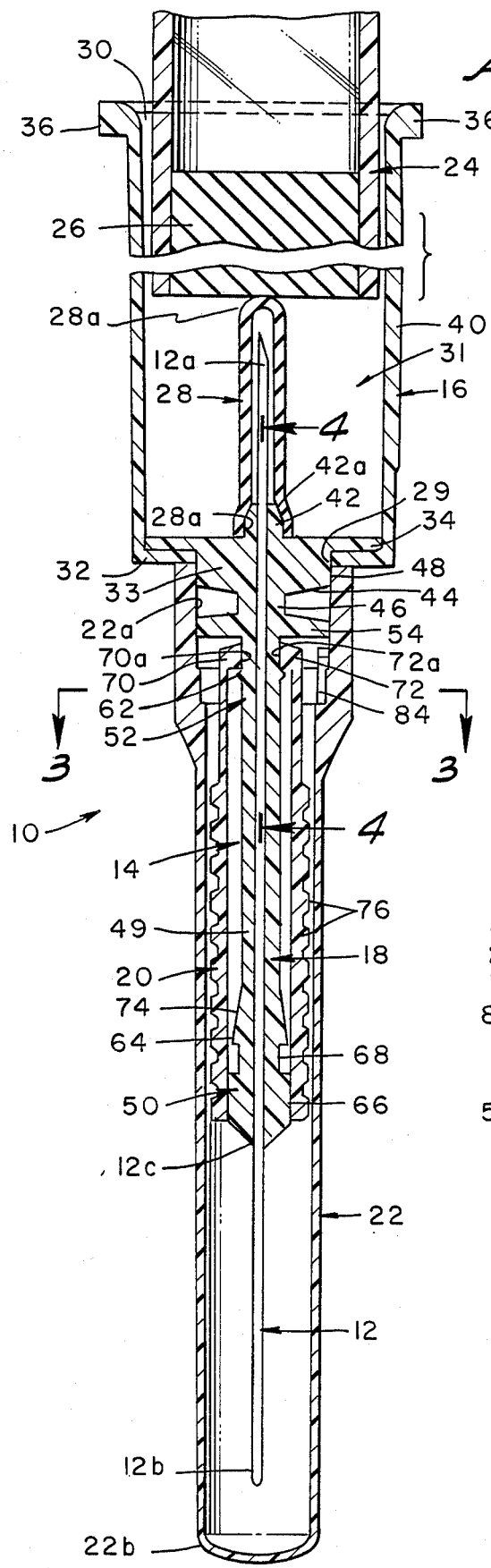
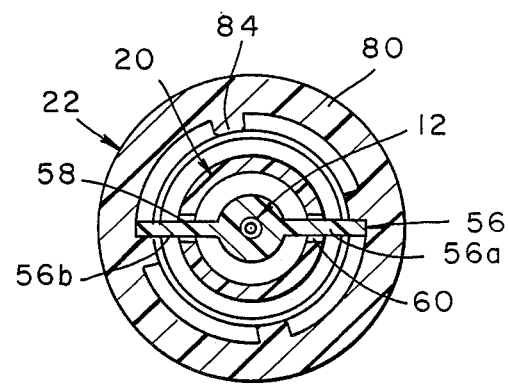
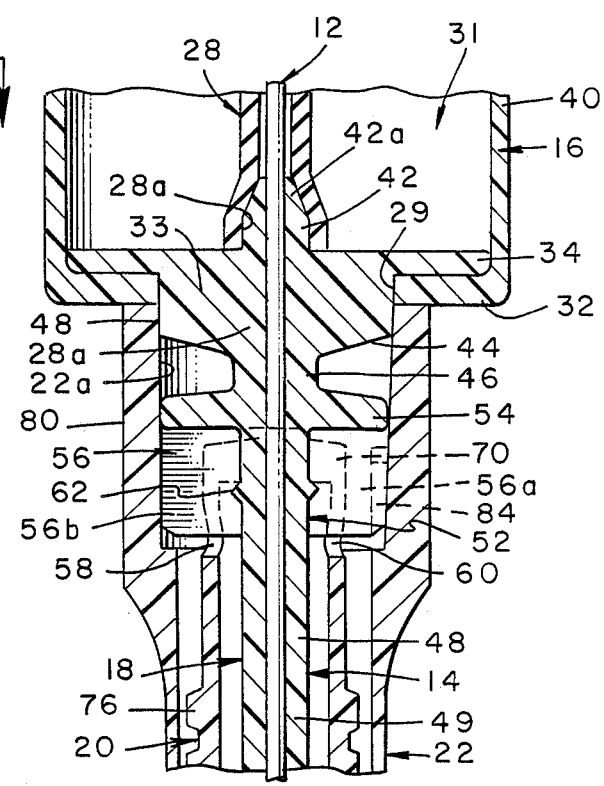

BLOOD WITHDRAWAL DEVICE WITH MOVABLE NEEDLE GUARD MEMBER

BACKGROUND OF THE INVENTION

1. Field of the Invention

This invention relates to blood withdrawal devices of the type which employ a sealed vacuum tube, and particularly, a device of this type equipped with a guard member that protects against accidental needle sticks.

2. Background Discussion

In U.S. patent application Ser. No. 07/035,434, entitled, "Medical Device", filed Ap. 7, 1987, assigned to the same assignee of this application, there is disclosed a blood withdrawal device equipped with a needle guard. This device is used with a sealed vacuum tube that is inserted in a tube holding section having a needle recessed within this section. Upon insertion of the sealed end of the tube into the tube holding section, the needle tip punctures the seal and allows blood to flow through the needle into the tube. The other end of the needle has already been inserted into the body of the patient and the vacuum in the tube sucks the blood from the patient so that the blood flows through the hollow shaft of the needle into the tube.

The portion of the needle extending outwardly from the tube holder section is equipped with a guard. The needle has a locking element attached to the needle shaft extending from the tube holding section and the guard is mounted on the shaft. The guard is movable axially between a retracted position where the tip of the needle is exposed so that it may be inserted into the body of the patient and a forward position where the guard covers the tip of the needle. Upon withdrawing the needle from the body of the patient, the guard is moved forward to cover the tip and prevent accidental needle sticks. The locking element along the needle shaft permanently locks the guard in the forward position.

In U.S. patent application Ser. No. 07/037,325, entitled,"Medical Device", filed Apr. 13, 1987, and assigned to the same assignee as this patent application, there is disclosed an improvement in the locking element. There is a problem in mounting the locking element to the shaft of the needle and the Medical Device disclosed in the '325 patent application overcomes this problem. The solution provided is to employ a locking member that has an elongated stem made of a polymeric material and this stem is bonded to the needle shaft during molding. As the stem is being formed about the needle shaft, pressure is applied to the molten plastic material which, upon cooling, shrinks and bonds the surface of the shaft of the needle to the stem.

SUMMARY OF THE INVENTION

The present invention is a combination of the advantageous features of the medical devices disclosed in the above-identified, prior filed, patent applications. (Both of these prior filed patent applications are incorporated herein by reference and made a part of this patent application.) The present invention provides a blood withdrawal device having a locking member bonded to the needle shaft with the tube holder and the locking member being a unitary structure.

There are several features of this invention, no single one of which is solely responsible for its desirable attributes. These features are disclosed in the following section of this patent application entitled "DESCRIPTION OF THE PREFERRED EMBODIMENT". dr

BRIEF DESCRIPTION OF THE DRAWING

The blood withdrawal device of this invention is illustrated in the drawing, with like numerals indicating like parts, and in which:

FIG. 2 is a cross-sectional view of the blood withdrawal device of this invention.

FIG. 3 is a cross-sectional view taken along line 3—3 of FIG. 2.

FIG. 4 is a cross-sectional view taken along line 4—4 of FIG. 2.

DESCRIPTION OF THE PREFERRED EMBODIMENT

Figure 1:
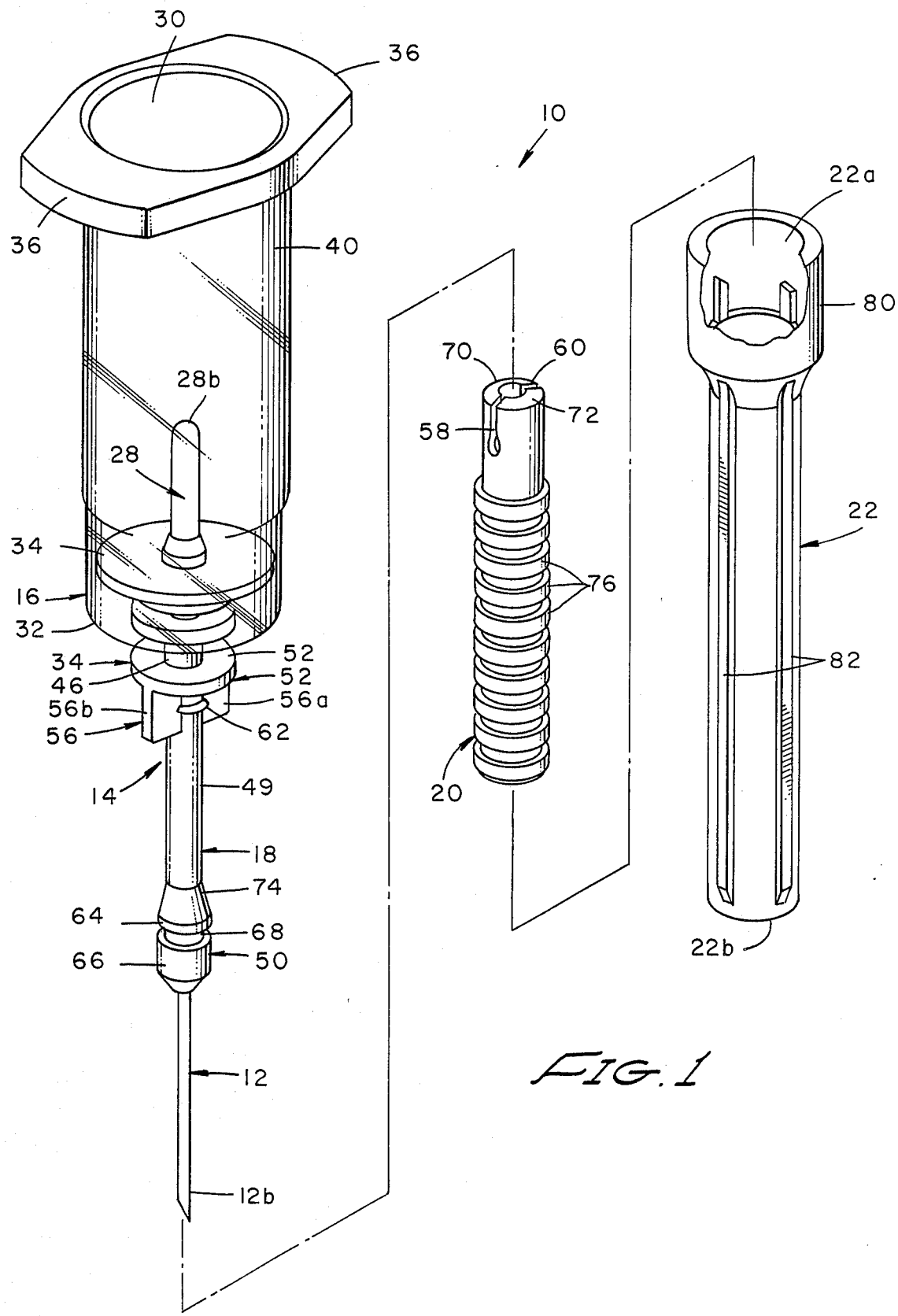
FIG. 1 is an exploded perspective view of the blood withdrawal device of this invention.

As best illustrated in FIG. 1, the blood withdrawal device 10 of this invention includes (a) a needle 12 (b) a unitary structure 14 including a tube holder section 16, (c) a guard locking section 18, (d) a needle guard 20, and (e) a sheath 22 for covering the needle.

FIG. 2 shows the device 10 with the sheath 22 removably connected to the tube holder section 16 and the needle guard 20 in a retracted position. Removal of the sheath 22 allows the needle 12 to be inserted into the body of the patient. With the needle 12 in the body of the patient, a vacuum collection tube 24 is inserted into the tube holder section 16 and moved inwardly to initiate the withdrawal of blood upon the rubber seal 26 of the tube being punctured by the needle.

The needle 12 is an elongated tubular member made of stainless steel. Typically the overall length of the needle will be from about 3.25 to about 4.5 inches with the opposed ends 12a and 12b of the shaft of the needle being truncated so that both ends of the needles will be sharp and adapted to pierce an object. The exposed length of the needle, i.e., from 12c to 12b is about 1 to about 1.5 inches. The one end 12b of the needle 12 is adapted to be inserted into the body of the patient. The other end 12a of the needle 12 is covered by a self sealing rubber cap 28 that acts as a valve. The cap 28 has an open end 28a and a closed end 28b. The cap 28 is compressed as the tube 24 moves into the tube holder section 16, with the end 12a of the needle piercing the end 28b. As illustrated in FIG. 2, as the vacuum collection tube 24 is inserted into the tube holder section 16 and moved inwardly towards the tip 12a of the needle 12, this tip 12a will penetrate the seal 26 of the vacuum tube, whereupon blood will flow from the patient through the hollow shaft of the needle into the collection tube.

In accordance with this invention, the tube holder section 16 and the guard locking section 18 are integral and made of a polymeric material, forming the unitary structure 14. This unitary structure 14 is made by sonically welding the tube holder section 16 to the guard locking section 18. The guard locking section 18 has the needle 12 firmly bonded in position. This is achieved during the molding process where the needle is inserted into the cavity of a mold, gripped, and held in position so it will not bow or move as molten polymeric material is injected in the cavity of the mold to form the unitary structure. Upon cooling, the molten material shrinks so that the guard locking section 18 is bonded firmly to the surface of the needle.

The tube holding section 16 includes a generally hollow cylindrical side wall 29 having an open end 30 adapted to receive the collection tube 24 and a base 32 opposite the open end. Opposite this open end 30 is an orifice 29 in the base 32 through which the guard locking section 18 passes. The cylindrical sidewall 29 and base 32 of tube holding section 16 provide a tube holding compartment 31 into which the tube 24 fits snugly but may slide in or out. Surrounding the open end 30 are a pair of outwardly extending flanges 36 that allow the user to grip the tube holder section 16 between the index finger and middle finger so that the user, by applying pressure to the end of the collection tube 24 with his or her thumb, can force the tube inwardly towards the tip 12a of the needle 12.

The locking section 18 has a disk-like mounting section 34 that rests on the base 32. In the manufacture of the device 10, the locking section 18 is placed in the position shown in FIG. 2 and then welded in place using ultrasonic sound waves to bond section 34 to the base 32. An outwardly extending cap holder member 42 having a cylindrical configuration and an inwardly tapered end 42a holds the cap 28. This end 42a is inserted into the open end 28a of the cap 28 and has a diameter slightly larger than the open end of the cap so that this end 28a expands outwardly and then firmly grips the cap holder 42.

Integral with the mounting section 34 is a plug 33 which fits into the orifice 29. The bottom of the plug 33 has an outwardly tapered bottom wall 44. A junction piece 46 extends outwardly from this bottom wall 44, and the bottom wall is offset slightly from the base by an outwardly tapered side wall 48. This outwardly tapered side wall 48 has a diameter approximately equal to the diameter of the open mouth 22a of the sheath 22, enabling the sheath to be force fitted onto the mounting section 34 to cover the end 12b of the needle 12 prior to use.

The guard locking section 18 includes an elongated stem 48 having a locking member 50 at one end and a guard mounting section 52 at the other end. The guard mounting section 52 includes an annular platform 54 which is integral with the junction piece 46. Extending outwardly at right angles to this annular platform 54 is a planar member 56 having two opposed flat surfaces 56a and 56b. This planar member 56 is inserted into opposed slits 58 and 60 in one end of the guard 20. Adjacent the platform is an annular rib 62 which runs about the circumference of the stem. This rib is used to hold the guard 20 in the retracted position prior to moving it forward to cover the tip 12b of the needle 12.

The locking member 50 includes two spaced apart shoulder elements 64 and 66 which have between them a recess in the form of an annular groove 68. This groove 68 coacts with a pair of collar members 70 and 72 at the one end of the guard. One shoulder 64 has a ramp section 74 which permits the collars members 70 and 72 to slide up the ramp, expand outwardly, and then snap into a locked position in the groove 68.

The guard 20 is a cylindrical member having at one end the collar members 70 and 72 formed by the two opposed teardrop slits 58 and 60. Each collar member has a finger element 70a and 70b, respectively, which is received in the groove 68 when the guard 20 is moved to the forward position. The exterior of the guard 20 has a series of raised ring elements 76 which facilitate gripping the guard.

The sheath 22 is designed to fit over the assembly of guard 20 and guard locking section 18 and abut the base 32 of the tube holder section 16. This sheath 22 has an open end 22a and a closed end 22b with the open end 22a being formed by outwardly tapering cylindrical wall 80 which slides over the annular platform 54 and the bottom wall 44 of the tube holder section 18. The annular platform 54 is displaced inwardly slightly relative to the bottom wall 44 to accommodate the taper of the open mouth 22a of the sheath 22. External splines 82 on the surface of the sheath 22 assist in gripping the sheath when it is to be removed. Internal splines 84 on the inside surface of the wall 82 may be present, but are optional.

Substantial cost savings are provided by employing the unitary structure 14. This structure 14 has the needle 12 firmly embedded in it so that the needle will not slip or move relative to the unitary structure 14. To form the guard locking section 18 about the shaft of the needle 12, the needle is placed in the cavity of the mold (not shown) and molten polymeric material is forced under pressure into the mold cavity while the needle is gripped by pins (not shown). Conventional insert molding techniques may be used and any polymeric material suitable for use with devices of this type may be employed. On cooling the molten plastic shrinks, so that the stem 48 firmly grips the shaft of the needle 12.

OPERATION

The blood withdrawal device 10 of this invention is simple to use, and provides the safety feature of guarding against accidental needle sticks. The sheath 22 is first removed and the one end 12b of the needle 12 is inserted into the body of the patient. Next the user inserts the vacuum collection tube 24 into the open end 30 of the tube holder section 16 moving it inwardly. As the tube 24 advances, the other end 12a of the needle 12 penetrates the seal 26 of the tube 24, with the tube depressing the cap 28 as it moves towards the mounting section 34. The inward movement of the tube 24 is stopped upon the seal 26 engaging the end of the cylindrical wall 38. As the end 12a of the needle 12 penetrates the seal 26, blood is sucked through the hollow shaft of the needle 12 into the tube 24. The cap 28 is depressed, but springs back to the position shown in FIG. 2 when the tube 24 is withdrawn. Upon the tube 24 being filled, the user grasps the guard 20 with one hand and pulls the device 10 outwardly away from the body of the patient. This moves the guard 20 forward so that the fingers 70a and 72a of the collar element are moved opposite the groove 68 and snap into position in the groove to lock the guard permanently in position. The sheath 22 may be replaced and the entire assembly discarded, or the sheath may not be replaced, since the guard 20 is in position protecting the end 12b of the needle.

SCOPE OF THE INVENTION

The above description presents the best mode contemplated of carrying out the present invention. This invention, however, is susceptible to modifications and alternate constructions from the embodiment shown in the drawing and described above. Consequently, it is not the intention to limit this invention to the particular embodiment disclosed. On the contrary, the intention is to cover all modifications and alternate constructions coming within the spirit and scope of the invention as generally expressed by the claims.

I claim:

1. A medical device of the type used to withdraw blood or other fluids from a patient into a vacuum tube having a seal in an open end, said seal being adapted to be penetrated by a needle, including an elongated needle having a hollow shaft terminating at a first end and a first open tip adapted to penetrate the body of a patient and a second end opposite said first end and terminating in a second open tip adapted to penetrate the seal of said tube, a unitary structure including (a) tube holding means having an open end into to which the tube is inserted during use and a cavity which receives the sealed end of the tube, said second end of the needle extending into the cavity but displaced inwardly from said open end in the tube holding means, and said first end of the needle extending outwardly from the tube holding means, (b) locking means bonded to the portion of the shaft of needle extending outwardly from the tube holding means, and including an elongated stem member made of a polymeric material through which a substantial portion of said shaft extends, said stem being bonded to the shaft during molding, with the stem being formed about the needle shaft by application of pressure to the molten polymeric material which, upon cooling, shrinks and bonds to the surface of said shaft; and a guard member carried on the portion of the shaft extending outwardly from the tube holding means and movable axially along said shaft between a first position where the guard member is inwardly from said first tip to enable said first tip to penetrate the body of a patient and a second position where the guard member covers said tip to prevent accidental needle sticks, said locking member permanently locking the guard member into position upon movement of said guard member from said first position to said second position.

2. The medical device of claim 1 wherein the locking means includes a groove and the guard member includes collar means which locks into said groove.

3. The medical device of claim 2 wherein the second open tip of the needle is covered with a self-sealing cap 4. The medical device of claim 1 including mounting means at the junction where the tube holding means and locking means meet and sheath means removably attached at said junction.

5. The medical device of claim 1 wherein the tube holding means is sonically welded to the locking means to form the unitary structure.

* * * * *